US00PP33693P2

(12) United States Plant Patent
van Sambeek

(10) Patent No.: US PP33,693 P2
(45) Date of Patent: Nov. 23, 2021

(54) ***GAILLARDIA* PLANT NAMED 'DOGAILSPINORHALIMP'**

(50) Latin Name: *Gaillardia aristata*
Varietal Denomination: Dogailspinorhalimp

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/203,014

(22) Filed: Mar. 16, 2021

(51) Int. Cl.
*A01H 5/02* (2018.01)
*A01H 6/14* (2018.01)

(52) U.S. Cl.
USPC ..... Plt./431

(58) Field of Classification Search
USPC ..... Plt./431, 226
CPC ... A01H 5/02; A01H 5/00; A01H 5/10; A01H 6/14
See application file for complete search history.

*Primary Examiner* — June Hwu
(74) *Attorney, Agent, or Firm* — C. Anne Whealy

(57) ABSTRACT

A new and distinct cultivar of *Gaillardia* plant named 'Dogailspinorhalimp', characterized by its compact and mounded plant habit; freely branching habit; dense and bushy habit; strong leaves that resist yellowing; early and freely flowering habit; single-type inflorescences; ligulate-shaped ray florets that are red to reddish orange in color with emarginate bright yellow-colored apices; and good garden performance.

1 Drawing Sheet

Botanical designation: *Gaillardia aristata.*
Cultivar denomination: 'DOGAILSPINORHALIMP'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Jan. 13, 2021, application number 2021/0126. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Gaillardia* plant, botanically known as *Gaillardia aristata* and hereinafter referred to by the name 'Dogailspinorhalimp'.

The new *Gaillardia* plant is a product of a planned breeding program conducted by the Inventor in Aalsmeer, The Netherlands. The objective of the breeding program is to create new compact *Gaillardia* plants with unique and attractive inflorescences and healthy leaves.

The new *Gaillardia* plant originated from an open-pollination in July, 2016 of a proprietary selection of *Gaillardia aristata* identified as code number GA15-000025-001, not patented, as the female, or seed, parent with an unknown proprietary selection of *Gaillardia aristata* as the male, or pollen, parent. The new *Gaillardia* plant was discovered and selected by the Inventor as a single flowering plant from within the progeny of the stated open-pollination in a controlled environment in Aalsmeer, The Netherlands in July, 2017.

Asexual reproduction of the new *Gaillardia* plant by vegetative terminal cuttings in a controlled environment in Aalsmeer, The Netherlands, since August, 2017 has shown that the unique features of this new *Gaillardia* plant are stable and reproduced true to type in successive generations.

SUMMARY OF THE INVENTION

Plants of the new *Gaillardia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dogailspinorhalimp'. These characteristics in combination distinguish 'Dogailspinorhalimp' as a new and distinct *Gaillardia* plant:

1. Compact and mounded plant habit.
2. Freely branching habit; dense and bushy habit.
3. Strong leaves that resist yellowing.
4. Early and freely flowering habit.
5. Single-type inflorescences.
6. Ligulate-shaped ray florets that are red to reddish orange in color with emarginate bright yellow-colored apices.
7. Good garden performance.

Plants of the new *Gaillardia* differ primarily from plants of the female parent selection in flowering habit as plants of the new *Gaillardia* are more freely flowering than plants of the female parent selection.

Plants of the new *Gaillardia* can be compared to plants of *Gaillardia* x *grandiflora* 'Kiegalpea', disclosed in U.S. Plant Pat. No. 20,717. In side-by-side comparisons, plants of the new *Gaillardia* differ from plants of 'Kiegalpea' in ray floret color as ray florets of plants of the new *Gaillardia* are red to reddish orange in color with emarginate bright yellow-colored apices whereas ray florets of plants of 'Kiegalpea' are yellow in color with an orange-colored ring.

Plants of the new *Gaillardia* can be also compared to plants of *Gaillardia* x *grandiflora* 'Kiegaldab', disclosed in U.S. Plant Pat. No. 20,718. In side-by-side comparisons, plants of the new *Gaillardia* differ from plants of 'Kiegaldab' in ray floret color as ray florets of plants of the new *Gaillardia* are red to reddish orange in color with emarginate bright yellow-colored apices whereas ray florets of plants of 'Kiegaldab' are dark burgundy and yellow bi-colored.

BRIEF DESCRIPTION OF THE PHOTOGRAPH

The accompanying colored photograph illustrates the overall appearance of the new *Gaillardia* plant showing the colors as true as it is reasonably possible to obtain in colored reproductions of this type. Colors in the photograph may differ slightly from the color values cited in the detailed botanical description which accurately describe the colors of the new *Gaillardia* plant. The photograph is a top perspective view of a typical flowering plant of 'Dogailspinorhalimp' grown in a container.

DETAILED BOTANICAL DESCRIPTION

The aforementioned photograph and following observations and measurements describe plants grown in 17-cm containers during the summer in an outdoor nursery in Aalsmeer, The Netherlands and under cultural practices typical of commercial *Gaillardia* production. During the production of the plants, day temperatures averaged 22° C. and night temperatures averaged 17° C. Plants were pinched one week after planting and were three months old when the photograph was taken and 28 weeks old when the description was taken. In the following description, color references are made to The Royal Horticultural Society Colour Chart, 2007 Edition, except where general terms of ordinary dictionary significance are used.

Botanical classification: *Gaillardia aristata* 'Dogailspinorhalimp'.

Parentage:

*Female, or seed, parent.*—Proprietary selection of *Gaillardia aristata* identified as code number GA15-000025-001, not patented.

*Male, or pollen, parent.*—Unknown proprietary selection of *Gaillardia aristata*, not patented.

Propagation:

*Type.*—Terminal vegetative cuttings.

*Time to initiate roots, summer.*—About twelve days at temperatures about 26° C.

*Time to initiate roots, winter.*—About two weeks at temperatures about 23° C.

*Time to produce a rooted young plant, summer.*—About two weeks at temperatures about 23° C.

*Time to produce a rooted young plant, winter.*—About 16 days at temperatures about 18° C.

*Root description.*—Medium in thickness, fibrous; typically white to light brown in color, actual color of the roots is dependent on substrate composition, water quality, fertilizer type and formulation, substrate temperature and physiological age of roots.

*Rooting habit.*—Moderately freely branching, medium density.

Plant description:

*Plant and growth habit.*—Herbaceous perennial; compact and mounded plant habit; moderately vigorous growth habit and rapid growth rate; freely branching habit with about eight primary branches each with about three secondary branches developing per plant; dense and bushy appearance.

*Plant height.*—About 23 cm.

*Plant width.*—About 33 cm.

*Lateral branch description.*—Length: About 21 cm. Diameter: About 8 mm. Internode length: About 3 cm. Strength: Strong. Aspect: Upright to about 20° from vertical. Texture and luster: Pubescent; glossy. Color: Close to 145A.

*Leaf description.*—Arrangement: Alternate, simple; sessile. Length: About 16 cm. Width: About 4.5 cm. Shape: Lanceolate. Apex: Acute. Base: Cuneate. Margin: Entire or occasionally with deep lobes. Texture and luster, upper and lower surfaces: Pubescent; semi-glossy. Venation pattern: Pinnate. Color: Developing leaves, upper and lower surfaces: Close to 138A. Fully developed leaves, upper surface: Close to 138A; venation, close to 138C. Fully developed leaves, lower surface: Close to 138A; venation, close to 138A.

Inflorescence description:

*Appearance.*—Single inflorescence form with ray and disc florets; inflorescences held mostly upright on strong peduncles; ray and disc florets develop acropetally on a capitulum.

*Fragrance.*—Faintly fragrant; pleasant.

*Flowering response.*—Plants begin flowering about 16 weeks after planting; plants flower naturally during June and July in The Netherlands.

*Postproduction longevity.*—Inflorescences maintain good substance for about eight to ten weeks on the plant; inflorescences not persistent.

*Quantity of inflorescences.*—Freely flowering habit, about 60 inflorescences develop per plant during the flowering season.

*Inflorescence size.*—Diameter: About 6 cm to 8 cm. Height: About 2 cm. Disc diameter: About 1.5 cm to 3 cm.

*Receptacles.*—Height: About 4 mm. Diameter: About 4 mm. Color: Close to 158A.

*Inflorescence buds.*—Height: About 1 cm. Diameter: About 2 cm. Shape: Button-shaped. Texture and luster: Smooth, glabrous; matte. Color: Close to 144A.

*Ray florets.*—Quantity per inflorescence: About 19 ray florets arranged in a single whorl. Length: About 2.3 cm to 3.5 cm. Width: About 1.5 cm to 2 cm. Shape: Ligulate. Apex: Emarginate with about three acute apices. Base: Acuminate. Margin: Entire; not undulate. Aspect: Horizontal to slightly upright. Texture and luster, upper surface: Smooth, glabrous; semi-glossy. Texture and luster, lower surface: Pubescent; semi-glossy. Color: When opening, upper surface: Towards the base, close to 46A; mid-section, close to 46B; towards the apex, close to 15A. When opening, lower surface: Towards the base, close to 47A and towards the apex, close to 15A. Fully opened, upper surface: Towards the base, close to 46A; mid-section, close to 42A; towards the apex, close to 15A; venation, similar to lamina colors; mid-section color becoming closer to 31A with development. Fully opened, lower surface: Towards the base, close to 47A and towards the apex, close to 15A; venation, close to 183A; with development, colors becoming closer to 47B towards the base; mid-section, close to 173B; and distally, close to 15A.

*Disc florets.*—Quantity per inflorescence: About 128 massed at the center of the receptacle in about eight whorls. Length: About 1 cm. Diameter: About 2 mm. Shape: Fused tubular. Apex: Acuminate. Texture and luster, inner surface: Pubescent; glossy. Texture and luster, outer surface: Smooth, glabrous; glossy. Color: When opening, inner and outer surfaces: Close to 9A; towards the apex, darker than 185A. Fully opened, inner and outer surfaces: Close to 170A; towards the apex, darker than 185A.

*Involucral bracts.*—Quantity per inflorescence: About 34 arranged in about three whorls. Length: About 1.7 cm. Width: About 6 mm. Shape: Elliptic. Apex: Acuminate. Base: Truncate. Margin: Entire. Texture and luster, upper and lower surfaces: Pubescent; semi-glossy. Color, upper and lower surfaces: Close to 138A.

*Peduncles.*—Length: About 6.5 cm. Diameter: About 3 mm. Strength: Moderately strong. Texture and luster: Pubescent; glossy. Color: Close to 145A.

*Reproductive organs.*—Androecium: Present on disc florets only. Quantity per floret: Five. Filament length: About 4 mm. Filament color: Close to 155D. Anther size: About 1 mm by 4 mm. Anther shape: Rectangular with a triangular apex. Anther color: Close to 15A; towards the apex, close to 187A. Pollen amount: Abundant. Pollen color: Close to 17A. Gynoecium: Present on disc florets only. Quantity per floret: One. Pistil length: About 1 cm. Stigma diameter: About 3 mm. Stigma shape: Two-lobed, plumose. Stigma color: Close to 185A. Style length: About 5 mm. Style color: Close to 155D. Ovary color: Close to 155D.

*Seeds and fruits.*—To date, seed and fruit production have not been observed on plants of the new *Gaillardia.*

Pathogen & pest resistance: To date, plants of the new *Gaillardia* have not been observed to be resistant to pathogens and pests common to *Gaillardia* plants.

Garden performance: Plants of the new *Gaillardia* have been observed to have good garden performance and to tolerate wind and rain and temperatures ranging from about −37° C. to about 30° C.

It is claimed:

1. A new and distinct *Gaillardia* plant named 'Dogailspinorhalimp' as illustrated and described.

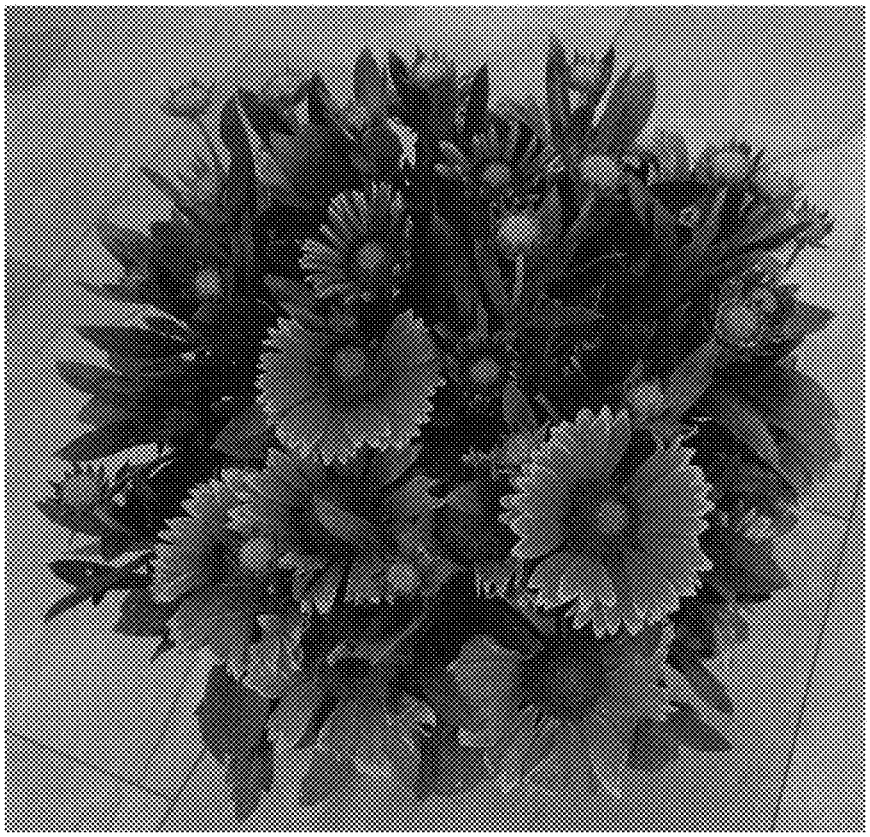

* * * * *